United States Patent [19]

Neuzil et al.

[11] Patent Number: 4,483,980

[45] Date of Patent: Nov. 20, 1984

[54] PROCESS FOR SEPARATING GLUCOSE FROM POLYSACCHARIDES BY SELECTIVE ADSORPTION

[75] Inventors: Richard W. Neuzil, Downers Grove; James W. Priegnitz, Elgin, both of Ill.

[73] Assignee: UOP Inc., Des Plaines, Ill.

[21] Appl. No.: 532,248

[22] Filed: Sep. 14, 1983

Related U.S. Application Data

[60] Continuation-in-part of Ser. No. 374,819, May 4, 1982, Pat. No. 4,442,285, which is a division of Ser. No. 197,874, Oct. 17, 1980, Pat. No. 4,349,668, which is a continuation-in-part of Ser. No. 690,769, May 27, 1976, abandoned.

[51] Int. Cl.³ .............................................. C07H 1/06
[52] U.S. Cl. ..................................... 536/127; 536/124
[58] Field of Search ......................... 536/1.1, 124, 127

[56] References Cited

U.S. PATENT DOCUMENTS 4,014,711 3/1977 Odawara et al. ...................... 127/46
4,349,668 9/1982 Neuzil et al. ......................... 536/124

Primary Examiner—Johnnie R. Brown
Attorney, Agent, or Firm—James R. Hoatson, Jr.; Louis A. Morris; William H. Page, II

[57] ABSTRACT

A process for the recovery of glucose from an aqueous mixture of glucose and polysaccharides. The mixture is contacted with an X zeolite containing potassium cations at exchangeable cationic sites and selectively adsorbing glucose in the zeolite. The polysaccharides are removed from the zeolite and the adsorbed glucose recovered by means of a desorbent liquid. Preferred systems for effecting the process are countercurrent and co-current simulating moving beds.

7 Claims, 4 Drawing Figures

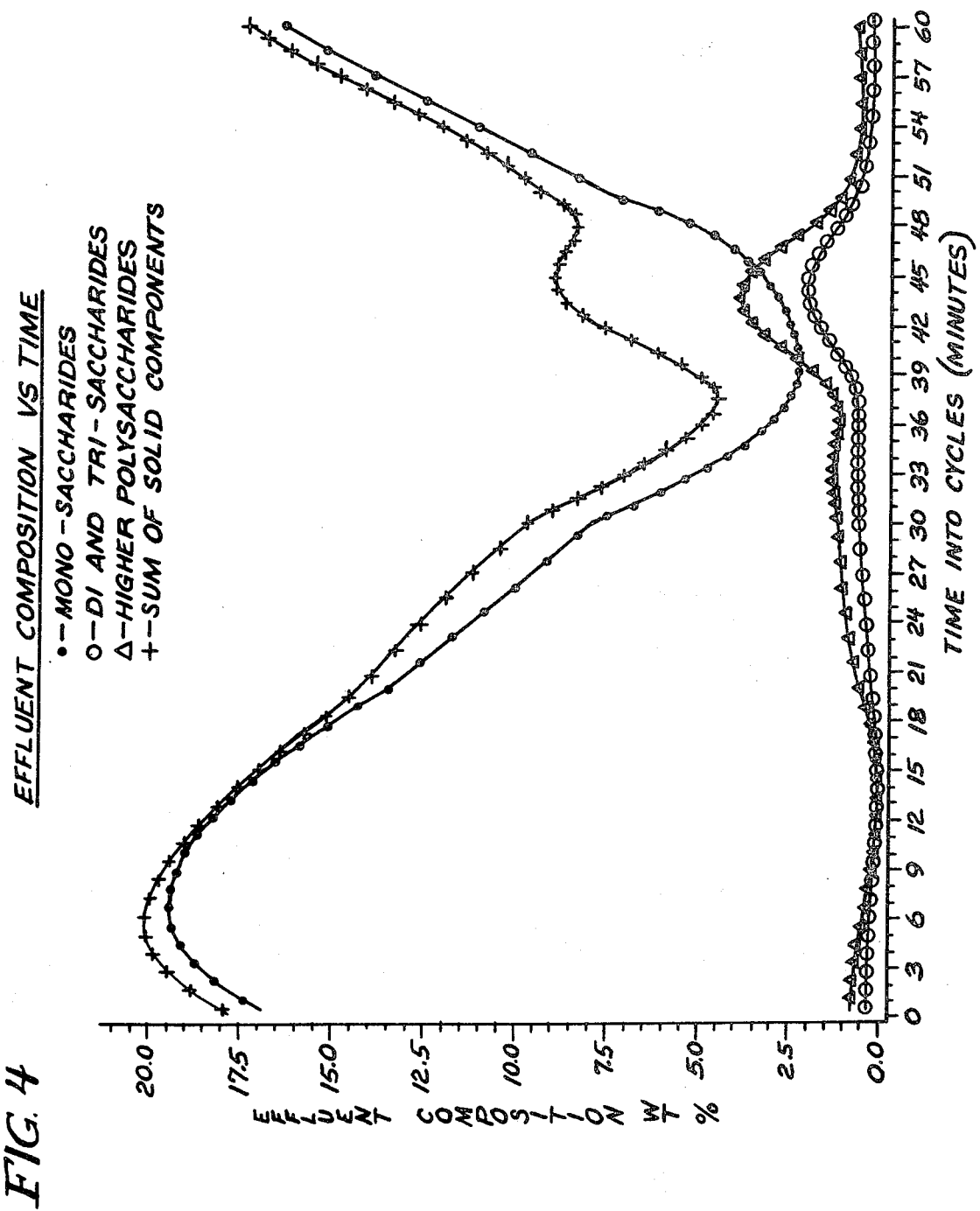

PROCESS FOR SEPARATING GLUCOSE FROM POLYSACCHARIDES BY SELECTIVE ADSORPTION

CROSS REFERENCE TO RELATED APPLICATIONS

This application is a continuation-in-part of our prior copending application Ser. No. 374,819, filed May 4, 1982, now U.S. Pat. No. 4,442,285, which is a division of our prior copending application Ser. No. 197,874, filed Oct. 17, 1980 and issued as U.S. Pat. No. 4,349,668, which is a continuation-in-part of our prior copending application Ser. No. 690,769, filed May 27, 1976 and now abandoned, all said prior applications incorporated herein by reference.

BACKGROUND OF THE INVENTION

Field of the Invention

The field of art to which this invention pertains is the solid-bed adsorptive separation of monosaccharides. More specifically the invention relates to a process for separating glucose from a mixture comprising glucose and polysaccharides which process employs an adsorbent comprising a crystalline aluminosilicate which selectively adsorbs glucose from the feed mixture.

BACKGROUND INFORMATION

It is known in the separation art that certain crystalline aluminosilicates referred to as zeolites can be used in the separation of a component from an aqueous solution of a mixture of different components. For example, adsorbents comprising aluminosilicates are used in the method described in U.S. Pat. No. 4,014,711 to separate fructose from a mixture of sugars in aqueous solution including fructose and glucose.

Our invention relates to the separation of nonhydrocarbons and more specifically to the separation of monosaccharides. We have surprisingly discovered that an adsorbent comprising an X zeolite containing potassium cations at the exchangeable cationic sites not only exhibits adsorptive selectivity for glucose with respect to polysaccharides but also uniquely has a large capacity for glucose in the presence of water, thereby making separation of glucose from a mixture comprising glucose and polysaccharides by solid-bed selective adsorption practical. On other adsorbents water is selectively retained over the glucose. Glucose (dextrose) is widely used in confectionery and baking industries, in canning of fruits and vegetables, in beverages and other products requiring sweeteners, and for the preparation of caramel color. In some instances it is used directly as replacement, wholly or in part, for cane or beet sugar; in other instances the special properties of glucose are utilized. Glucose is readily manufactured from starch (which is made up exclusively of glucose units) by hydrolysis with mineral acids at elevated temperature followed by refining and crystallization of the hydrolyzate. Complete separation of glucose from water soluble polysaccharides by conventional methods is, however, very difficult. The present invention enables such separation.

SUMMARY OF THE INVENTION

It is accordingly a broad objective of our invention to provide a process for separating glucose from a feed mixture containing glucose and polysaccharides to produce a glucose product stream containing a higher concentration of glucose than was contained in the feed mixture. More specifically, it is an objective of our invention to provide a process for separating glucose from a feed mixture, such as an invert sugar solution or a corn syrup, containing glucose and polysaccharides.

In brief summary, our invention is, in one embodiment, a process for separating glucose from a mixture thereof with polysaccharides, at separation conditions, with an X zeolite containing potassium cations at exchangeable cationic sites and selectively adsorbing glucose in the zeolite, removing the polysaccharides from the zeolite and thereafter recovering the adsorbed glucose from the zeolite by means of a desorbent liquid at desorption conditions.

Other objectives and embodiments of our invention encompass details about feed mixtures, adsorbents, desorbent materials, flow schemes and operating conditions all of which are hereinafter disclosed in the following discussion of each of the facets of the present invention.

BRIEF DESCRIPTION OF THE FIGURES

FIG. 4 comprises a graphical presentation of data obtained in a computer simulation of the high efficiency simulated moving bed embodiment of the process of the present invention and is discussed hereinafter in greater detail in this Illustrative Embodiment I.

DESCRIPTION OF THE INVENTION

Figure 1:
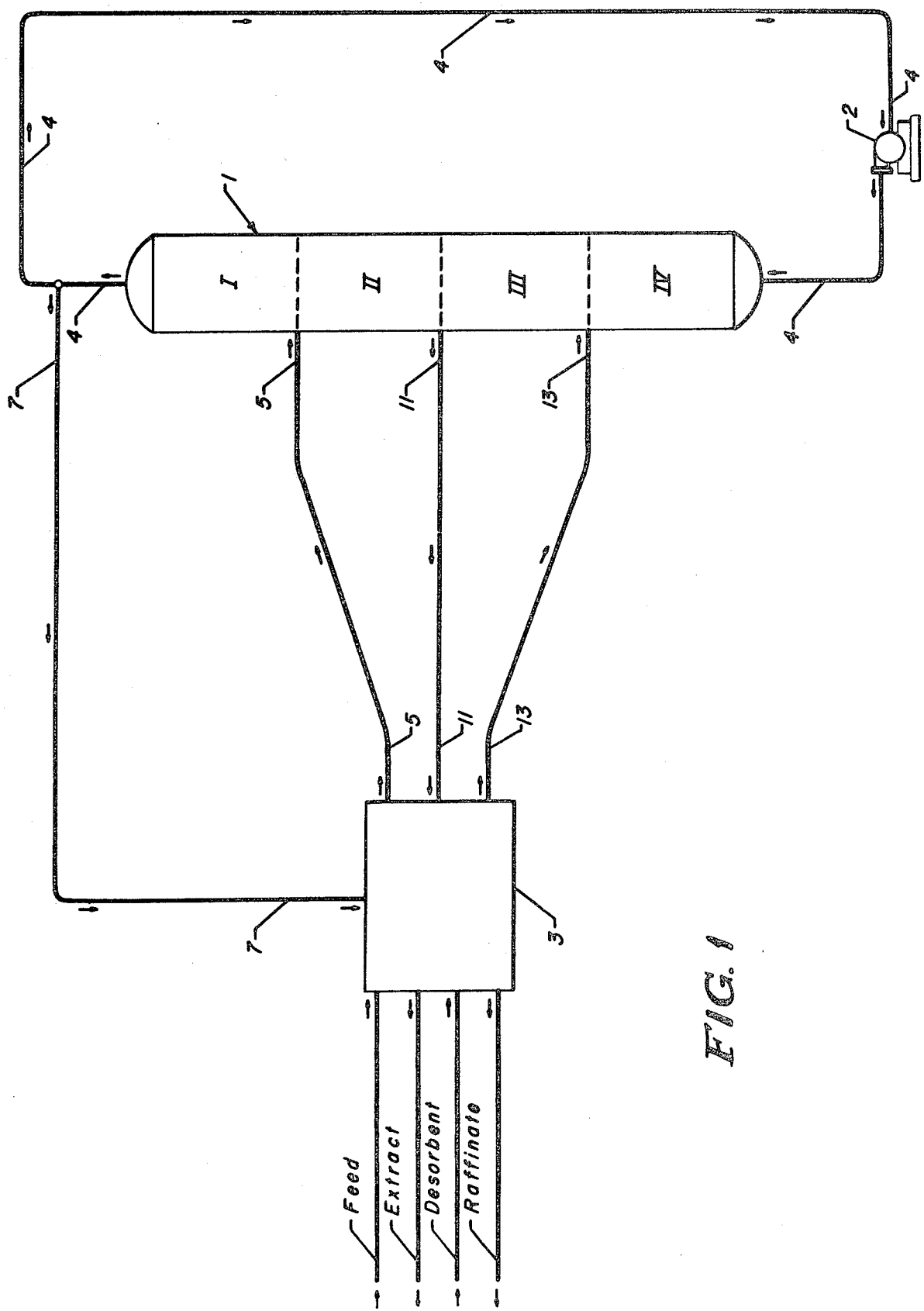
FIG. 1 represents, in schematic form, the embodiment of the present invention incorporating a countercurrent simulated moving bed, hereinafter described, including adsorption column 1, manifold system 3 and various interconnecting lines.

At the outset the definitions of various terms used throughout the specification will be useful in making clear the operation, objects and advantages of this process.

A "feed mixture" is a mixture containing one or more extract components and one or more raffinate components to be separated by this process. The term "feed stream" indicates a stream of a feed mixture which passes to the adsorbent used in the process.

An "extract component" is a component that is more selectively adsorbed by the adsorbent while a "raffinate component" is a component that is less selectively adsorbed. The term "desorbent material" shall mean generally a material capable of desorbing an extract component. The term "desorbent stream" or "desorbent input stream" indicates the stream through which desorbent material passes to the adsorbent. The term "raffinate stream" or "raffinate output stream" means a stream through which a raffinate component is removed from the adsorbent. The composition of the raffinate stream can vary from essentially 100% desorbent material to essentially 100% raffinate components. The term "extract stream" or "extract output stream" shall mean a stream through which an extract material which has been desorbed by a desorbent material is removed from the adsorbent. The composition of the extract stream, likewise, can vary from esssentially 100% desorbent material to essentially 100% extract components. At least a portion of the extract stream, and preferably at least a portion of the raffinate stream, from the separation process are passed to separation means, typically fractionators or evaporators, where at least a portion of desorbent material is separated to produce an extract product and a raffinate product. The term "extract product" and "raffinate product" mean products produced by the process containing, respectively, an extract component and a raffinate component in higher concentrations than those found in the extract stream and the raffinate stream.

The term "selective pore volume" of the adsorbent is defined as the volume of the adsorbent which selectively adsorbs an extract component from the feed mixture. The term "non-selective void volume" of the adsorbent is the volume of the adsorbent which does not selectively retain an extract component from the feed mixture. This volume includes the cavities of the adsorbent which contain no adsorptive sites and the interstitial void spaces between adsorbent particles. The selective pore volume and the non-selective void volume are generally expressed in volumetric quantities and are of importance in determining the proper flow rates of fluid required to be passed into an operational zone for efficient operations to take place for a given quantity of adsorbent. When adsorbent "passes" into an operational zone (hereinafter defined and described) employed in one embodiment of this process, its non-selective void volume, together with its selective pore volume, carried fluid into that zone. The non-selective void volume is utilized in determining the amount of fluid which should pass into the same zone in a countercurrent direction to the adsorbent to displace the fluid present in the non-selective void volume. If the fluid flow rate passing into a zone is smaller than the non-selective void volume rate of adsorbent material passing into that zone, there is a net entrainment of liquid into the zone by the adsorbent. Since this net entrainment is a fluid present in non-selective void volume of the adsorbent, it, in most instances, comprises less selectively retained feed components. The selective pore volume of an adsorbent can in certain instances adsorb portions of raffinate material from the fluid surrounding the adsorbent, since in certain instances there is competition between extract material and raffinate material for adsorptive sites within the selective pore volume. If a large quantity of raffinate material with respect to extract material surrounds the adsorbent, raffinate material can be competitive enough to be adsorbed by the adsorbent.

The so-called "simple sugars" are classified as monosaccharides and are those which upon hydrolysis do not break down into smaller simpler sugars. One may further classify monosaccharides as aldoses or ketoses, depending upon whether they are hydroxy aldehydes or hydroxy ketones, and by the number of carbon atoms in the molecule. Most common and well-known are probably the hexoses. Common ketohexoses are fructose (levulose) and sorbose; common aldohexoses are glucose (dextrose) mannose and galactose. The term "oligosaccharides", as commonly understood in the art and as used herein, means simple polysaccharides containing a known number of constituent monosaccharide units. An oligosaccharide that breaks up upon hydrolysis into two monosaccharide units is called a disaccharide, examples being sucrose, maltose, and lactose. Those giving three such units are trisaccharides, of which raffinose and melezitose are examples. Di-, tri-, and tetrasaccharides comprise practically all of the oligosaccharides. The term "polysaccharide" includes oligosaccharides but usually it refers to carbohydrate materials of much higher molecular weight, namely, those that are capable of breaking up upon hydrolysis into a large number of monosacchride units. Typical polysaccharides are starch, glycogen, cellulose and pentosans.

Desorbent materials used in various prior art adsorptive separation processes vary depending upon such factors as the type of operation employed. In the swing bed system, in which the selectively adsorbed feed component is removed from the adsorbent by a purge stream, desorbent selection is not as critical and desorbent material comprising gaseous hydrocarbons such as methane, ethane, etc., or other types of gases such as nitrogen or hydrogen, may be used at evaporated temperatures or reduced pressures or both to effectively purge the adsorbed feed component from the adsorbent. However, in adsorptive separation processes which are generally operated continuously at substantially constant pressures and temperatures to ensure liquid phase, the desorbent material must be judiciously selected to satisfy many criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity (hereinafter discussed in more detail), it is preferred that the adsorbent be more selective for all of the extract components with respect to a raffinate component than it is for the desorbent material with respect to a raffinate component. Secondly, desorbent material must be compatible with the particular adsorbent and the particular feed mixture. More specifically, they must not reduce or destroy the critical selectivity of the adsorbent for an extract component with respect to aa raffinate component. Additionally, desorbent materials should not chemically react with or cause a chemical reaction of either an extract component or a raffinate component. Both the extract stream and the raffinate stream are typically removed from the adsorbent in admixture with desorbent material and any chemical reaction involving a desorbent material and an extract component or a raffinate component would reduce the purity of the extract product or the raffinate product or both. Since both the raffinate stream and the extract stream typically contain desorbent material, desorbent materials should additionally be substances which are easily separable from the feed mixture that is passed into the process. Without a method of separating at least a portion of the desorbent material present in the extract stream and the raffinate stream, the concentration of an extract component in the extract product and the concentration of a raffinate component in the raffinate product would not be very high, nor would the desorbent material be available for reuse in the process. It is contemplated that at least a portion of the desorbent material will be separated from the extract and the raffinate streams by distillation or evaporation, but other separation methods such as reverse osmosis may also be employed alone or in combination with distillation or evaporation. Since the raffinate and extract products are foodstuffs intended for human consumption, desorbent material should also be non-toxic. Finally, desorbent materials should also be materials which are readily available and therefore reasonable in cost.

The prior art has recognized that certain characteristics of adsorbents are highly desirable, if not absolutely necessary, to the successful operation of a selective adsorption process. Such characteristics are equally important to this process. Among such characteristics are: adsorptive capacity for some volume of an extract component per volume of adsorbent; the selective adsorption of an extract component with respect to a raffinate component and the desorbent material; and sufficiently fast rates of adsorption and desorption of an extract component to and from the adsorbent. Capacity of the adsorbent for adsorbing a specific volume of an extract component is, of course, a necessity; without such capacity the adsorbent is useless for adsorptive separation. Furthermore, the higher the adsorbent's capacity for an extract component the better is the adsorbent. Increased capacity of a particular adsorbent makes it possible to reduce the amount of adsorbent needed to separate an extract component of known concentration contained in a particular charge rate of feed mixture. A reduction in the amount of adsorbent required for a specific adsorptive separation reduces the cost of a separation process. It is important that the good initial capacity of the adsorbent be maintained during actual use in the separation process over some economically desirable life. The second necessary adsorbent characteristic is the ability of the adsorbent to separate components of the feed; or, in other words, that the adsorbent possess adsorptive selectivity, (B), for one component as compared to another component. Relative selectively can be expressed not only for one feed component as compared to another but can also be expressed between any feed mixture component and the desorbent material. The selectivity, (B), is defined as the ratio of the two components of the adsorbed phase over the ratio of the same two components in the unadsorbed phase at equilibrium conditions. Relative selectivity is shown as Equation 1, below:

$$\text{Selectivity} = (B) = \frac{\text{vol. percent } C/\text{vol. percent } D_A}{\text{vol. percent } C/\text{vol. percent } D_U} \quad \text{Equation 1}$$

where C and D are two components of the feed represented in volume percent and the subscripts A and U represent the adsorbed and unadsorbed phases respectively. The equilibrium conditions were determined when the feed passing over a bed of adsorbent did not change composition after contacting the bed of adsorbent. In other words, there was no net transfer of material occurring between the unadsorbed and adsorbed phases. Where selectivity of two components approaches 1.0, there is no preferential adsorption of one component by the adsorbent with respect to the other; they are both adsorbed (or non-adsorbed) to about the same degree with respect to each other. As the (B) becomes less than or greater than 1.0, there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. Ideally, desorbent materials should have a selectivity equal to about 1 or slightly less than 1 with respect to all extract components so that all of the extract components can be desorbed as a class with reasonable flow rates of desorbent material and so that extract components can displace desorbent material in a subsequent adsorption step. While separation of an extract component from a raffinate component is theoretically possible when the selectivity of the adsorbent for the extract component with respect to the raffinate component is just slightly greater than 1.0, it is preferred that such selectivity be reasonably greater than 1.0. Like relative volatility, the higher the selectivity the easier the separation is to perform. Higher selectivities permit a smaller amount of adsorbent to be used. The third important characteristic is the rate of exchange of the extract component of the feed mixture material, or, in other words, the relative rate of desorption of the extract component. This characteristic relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process.

The adsorbent used in the process of this invention comprises a specific crystalline aluminosilicates or molecular sieve. Crystalline aluminosilicates such as that used in the present invention include crystalline aluminosilicate cage structures in which the alumina and silica tetrahedra are intimately connected in an open three dimensional network to form cage-like structures with window-like pores of about 8 Å free diameter. The tetrahedra are cross-linked by the sharing of oxygen atoms with spaces between the tetrahedra occupied by water molecules prior to partial or total dehydration of this zeolite. The dehydration of the zeolite results in crystals interlaced with cells having molecular dimensions and thus the crystalline aluminosilicates are often referred to as "molecular sieves," particularly when the separation which they effect is dependent essentially upon differences between the sizes of the feed molecules as, for instance, when smaller normal paraffin molecules are separated from larger isoparaffin molecules by using a particular molecular sieve.

In hydrated form, the crystalline aluminosilicates generally encompass those zeolites represented by the Formula 1 below:

$$M_{2/n}O:Al_2O_3:wSiO_2:yH_2O \qquad \text{Formula 1}$$

where "M" is a cation which balances the electrovalence of the aluminum-centered tetrahedra and which is generally referred to as an exchangeable cationic site, "n" represents the valence of the cation, "w" represents the moles of SiO$_2$, and "y" represents the moles of water. The generalized cation "M" may be monovalent, divalent or trivalent or mixtures thereof.

The prior art has generally recognized that adsorbents comprising X and Y zeolites can be used in certain adsorptive separation processes. These zeolites are described and defined in U.S. Pat. Nos. 2,882,244 and 3,130,007, respectively incorporated herein by reference thereto. The X zeolite in the hydrated or partially hydrated form can be represented in terms of mole oxides as shown in Formula 2 below:

$$(0.9 \pm 0.2)M_{2/n}O:Al_2O_3:(2.50 \pm 0.5)SiO_2:yH_2O \quad \text{Formula 2}$$

where "M" represents at least one cation having a valence of not more than 3, "n" represents the valence of "M," and "y" is a value up to about 9 depending upon the identity of "M" and the degree of hydration of the crystal. As noted from Formula 2, the $SiO_2/Al_2O_3$ mole ratio of X zeolite is $2.5 \pm 0.5$. The cation "M" may be one or more of a number of cations such as a hydrogen cation, an alkali metal cation, or an alkaline earth cation, or other selected cations, and is generally referred to as an exchangeable cationic site. As the X zeolite is initially prepared, the cation "M" is usually predominately sodium, that is, the major cation at the exchangeable cationic sites is sodium and the zeolite is therefore referred to as a sodium-X zeolite. Depending upon the purity of the reactants used to make the zeolite, other cations mentioned above may be present, however, as impurities. The Y zeolite in the hydrated or partially hydrated form can be similarly represented in the terms of mole oxides as in Formula 3 below:

$$(0.9 \pm 0.2)M_{2/n}O:Al_2O_3:wSiO_2:yH_2O \quad \text{Formula 3}$$

where "M" is at least one cation having a valence not more than 3, "n" represents the valence of "M," "w" is a value greater than about 3 up to about 6, and "y" is a value up to about 9 depending upon the identity of "M" and the degree of hydration of the crystal. The $SiO_2/Al_2O_3$ mole ratio for Y zeolites can thus be from about 3 to about 6. Like the X zeolite, the cation "M" may be one or more of a variety of cations but, as the Y zeolite is initially prepared, the cation "M" is also usually predominately sodium. A Y zeolite containing predominately sodium cations at the exchangeable cationic sites is therefore referred to as a sodium-Y zeolite.

Cations occupying exchangeable cationic sites in the zeolite may be replaced with other cations by ion exchange methods well known to those having ordinary skill in the field of crystalline alumino-silicates. Such methods are generally performed by contacting the zerolite or an adsorbent material containing the zeolite with an aqueous solution of the soluble salt of the cation or cations desired to be placed upon the zeolite. After the desired degree of exchange takes place, the sieves are removed from the aqueous solution, washed, and dried to a desired water content. By such methods the sodium cations and any non-sodium cations which might be occupying exchangeable sites as impurities in a sodium-X or sodium-Y zeolite can be partially or essentially completely replaced with other cations. The zeolite used in the process of this invention is an X-type zeolite ion exchanged with potassium cations at exchangeable cationic sites.

Typically, adsorbents used in separative processes contain zeolite crystals dispersed in an amorphous material, organic or inorganic matrix. The zeolite will typically be present in the adsorbent in amounts ranging from about 75 to about 98 wt.% based on volatile-free composition. Volatile-free compositions are generally determined after the adsorbent has been calcined at 900° C. in order to drive off all volatile matter. The remainder of the adsorbent will generally be the inorganic matrix material such as silica, titania, or alumina or mixtures thereof, or compounds, such as clays, which material is present in intimate mixture with the small particles of the zeolite material. Water permeable organic polymers such as cellulose acetate may also be useful. Inorganic oxide matrix material may be an adjunct of the manufacturing process for zeolite (for example, intentionally incomplete purification of either zeolite during its manufacture) or it may be added to relatively pure zeolite, but in either case its usual purpose is as a binder to aid in forming or agglomerating the hard crystalline particles of the zeolite. Normally, the adsorbent will be in the form of particles such as extrudates, aggregates, tablets, macrospheres or granules having a desired particle size range. The typical adsorbent will have a particle size range of about 16–60 mesh (Standard U.S. Mesh). Examples of zeolites used in adsorbents known to the art, either as is or after cation exchange, are "Molecular Sieves 13X" and "SK-40" both of which are available from the Linde Company, Tonawanda, N.Y. The first material of course contains X zeolite while the latter material contains Y zeolite.

The adsorbent may be employed in the form of a dense compact fixed bed which is alternatively contacted with the feed mixture and desorbent materials. In the simplest embodiment of the invention, the adsorbent is employed in the form of a single static bed in which case the process is only semi-continuous. In another embodiment, a set of two or more static beds may be employed in fixed bed contacting with appropriate valving so that the feed mixture is passed through one or more adsorbent beds while the desorbent materials can be passed through one or more of the other beds in the set. The flow of feed mixture and desorbent materials may be either up or down through the desorbent. Any of the conventional apparatus employed in static bed fluid-solid contacting may be used.

Moving bed or simulated moving bed flows systems, however, have a much greater separation efficiency than fixed adsorbent bed systems and are therefore preferred for use in this separation process. In the moving bed or simulated moving bed processes, the adsorption and desorption operations are continuously taking place which allows both continuous production of an extract and a raffinate stream and the continual use of feed and desorbent streams. One preferred embodiment of this process utilizes what is known in the art as the simulated moving bed countercurrent flow system. The operating principles and sequence of such a flow system are described in U.S. Pat. No. 2,985,589 incorporated herein by reference thereto. In such a system, it is the progressive movement of multiple liquid access points down an adsorbent chamber that simulates the upward movement of adsorbent contained in the chamber. Only four of the access lines are active at any one time: the feed input stream, desorbent inlet stream, raffinate outlet stream, and extract outlet stream access lines. Coincident with this simulated upward movement of the solid absorbent is the movement of the liquid occupying the void volume of the packed bed of adsorbent. So that countercurrent contact is maintained, a liquid flow down the adsorbent chamber may be provided by a pump. As an active liquid access point moves through a cycle, that is, from the top of the chamber to the bottom, the chamber circulation pump moves through different zones which require different flow rates. A programmed flow controller may be provided to set and regulate these flow rates.

The active liquid access points effectively divide the adsorbent chamber into separate zones, each of which has a different function. In this embodiment of this process, it is generally necessary that three separate operational zones be present in order for the process to take place although in some instances an optional fourth zone may be used.

There is a net positive fluid flow through all portions of the column in the same direction, although the composition and rate of the fluid will, of course, vary from point to point. With reference to FIG. 1, zones I, II, III and IV are shown as well as manifold system 3, pump 2, which maintains the net positive fluid flow, and line 4 associated with pump 2. Also shown and identified are the inlet and outlet lines to the process which enter or leave via manifold system 3.

The adsorption zone, zone I, is defined as the adsorbent located between the feed inlet streams and the raffinate outlet stream 7. In this zone, the feedstock contacts the adsorbent, an extract component is adsorbed, and a raffinate stream is withdrawn. Since the general flow through zone I is from the feed stream which passes into the zone to the raffinate stream which passes out of the zone, the flow in this zone is considered to be in a downstream direction when proceeding from the feed inlet to the raffinate outlet streams.

Immediately upstream with respect to fluid flow in zone I is the purification zone, zone II. The purification zone is defined as the adsorbent between the extract outlet stream 11 and the feed inlet streams. The basic operations taking place in zone II are the displacement from the non-selective void volume of the adsorbent of any raffinate material carried into zone II by the shifting of adsorbent into this zone and the desorption of any raffinate material adsorbed within the selective pore volume of the adsorbent or adsorbed on the surfaces of the adsorbent particles. Purification is achieved by passing a portion of extract stream material leaving zone III into zone II at zone II's upstream boundary, the extract outlet stream, to effect the displacement of raffinate material. The flow of material in zone II is in a downstream direction from the extract outlet stream to the feed inlet stream.

Immediately upstream of zone II with respect to the fluid flowing in zone II is the desorption zone, or zone III. The desorption zone is defined as the adsorbent between the desorbent inlet 13 and the extract outlet stream 11. The function of the desorption zone is to allow a desorbent material which passes into this zone to displace the contact with feed in zone I in a prior cycle of operation. The flow of fluid in zone III is essentially in the same direction as that of zones I and II.

In some instances, an optional buffer zone, zone IV, may be utilized. This zone, defined as the adsorbent between the raffinate outlet stream 7 and the desorbent inlet stream 13, if used, is located immediately upstream with respect to the fluid flow to zone III. Zone IV would be utilized to conserve the amount of desorbent utilized in the desorption step since a portion of the raffinate stream which is removed from zone I can be passed into zone IV to displace desorbent material present in that zone out of that zone into the desorption zone. Zone IV will contain enough adsorbent so that raffinate material present in the raffinate stream passing out of zone I and into zone IV can be prevented from passing into zone III, thereby contaminating the extract stream removed from zone III. In the instances in which the fourth operational zone is not utilized, the raffinate stream passing from zone I to zone IV must be carefully monitored in order that the flow directly from zone I to zone III can be stopped when there is an appreciable quantity of raffinate material present in the raffinate stream passing from zone I into zone III so that the extract outlet stream is not contaminated.

A cyclic advancement of the input and output streams through the fixed bed of adsorbent can be accomplished by utilizing a manifold system in which the valves in the manifold are operated in a sequential manner to effect the shifting of the input and output streams, thereby allowing a flow of fluid with respect to solid adsorbent in a countercurrent manner. Another mode of operation which can effect the countercurrent flow of solid adsorbent with respect to fluid involves the use of a rotating disc valve in which the input and output streams are connected to the valve and the lines through which feed input, extract output, desorbent input and raffinate output streams pass are advanced in the same direction through the adsorbent bed. Both the manifold arrangement and disc valve are known in the art. Specifically, rotary disc valves which can be utilized in this operation can be found in U.S. Pat. Nos. 3,040,777 and 3,422,848. Both of the aforementioned patents disclose a rotary type connection valve in which the suitable advancement of the various input and output streams from fixed sources can be achieved without difficulty.

In many instances, one operational zone will contain a much larger quantity of adsorbent than some other operational zone. For instance, in some operations the buffer zone can contain a minor amount of adsorbent as compared to the adsorbent required for the adsorption and purification zones. It can also be seen that in instances in which desorbent is used which can easily desorb extract material from the adsorbent, that a relatively small amount of adsorbent will be needed in a desorption zone as compared to the adsorbent needed in the buffer zone or adsorption zone or purification zone or all of them. Since it is not required that the adsorbent be located in a single column, the use of multiple chambers or a series of columns is within the scope of the invention.

It is not necessary that all of the input or output streams be simultaneously used, and in fact, in many instances some of the streams can be shut off while others effect an input or output of material. The apparatus which can be utilized to effect the process of this invention can also contain a series of individual beds connected by connecting conduits upon which are placed input or output taps to which the various input or output streams can be attached and alternatively and periodically shifted to effect continuous operation. In some instances, the connecting conduits can be connected to transfer taps which during the normal operations do not function as a conduit through which material passes into or out of the process.

It is contemplated that at least a portion of the extract output stream will pass into a separation means wherein at least a portion of the desorbent material can be separated to produce an extract product containing a reduced concentration of desorbent material. Preferably, but not necessary to the operation of the process, at least a portion of the raffinate output stream will also be passed to a separation means wherein at least a portion of the desorbent material can be separated to produce a desorbent stream which can be reused in the process and a raffinate product containing a reduced concentration of desorbent material. The separation means will typically be a fractionation column or an evaporator, the design and operation of either being well known to the separation art.

Reference can be made to D. B. Broughton U.S. Pat. No. 2,985,589, and to a paper entitled "Continuous Adsorptive Processing—A New Separation Technique" by D. B. Broughton presented at the 34th Annual Meeting of the Society of Chemical Engineers at Tokyo, Japan, on Apr. 2, 1969 (both of which are incorporated herein by reference), for further explanation of the simulated moving bed countercurrent process flow scheme.

Another embodiment of a simulated moving bed flow system suitable for use in the process of the present invention is the co-current high efficiency simulated moving bed process disclosed in our assignee's U.S. patent application Ser. No. 407,680, filed Aug. 12, 1982, now U.S. Pat. No. 4,402,832, incorporated by reference herein in its entirety. The essence of that embodiment is based on the plot of FIG. 2, where there is shown two overlapping curves, one, as indicated, being the concentration gradient of a relatively retained component through the system (hereinafter defined) and the second, as indicated, being the corresponding concentration gradient for the relatively nonretained or accelerated component. The retention or acceleration results, depending on the separation means in question, from the selective adsorption, volatility, diffusion or reaction to externally applied fields of the various components. The ordinate of the plot represents the magnitude of the concentration of a component at a point in question on the curve while the abscissa represents the position of that point in the system at a specific instant. The plot of FIG. 2 may be deemed indicative of the appearance of what the concentration gradients in a solid bed adsorptive system of a more selectively adsorbed component (component 1) and a less selectively adsorbed component (component 2) throughout a packed bed would be a given time after a slug of feed comprising a mixture of the components is introduced into the bed followed by a continuous flow of displacement fluid (desorbent) which is capable of effecting desorption of component 1 from the adsorbent. Components 1 and 2 separate at least partially because of the selective retention of component 1 resulting from the selective adsorption of component 1.

Figure 2:
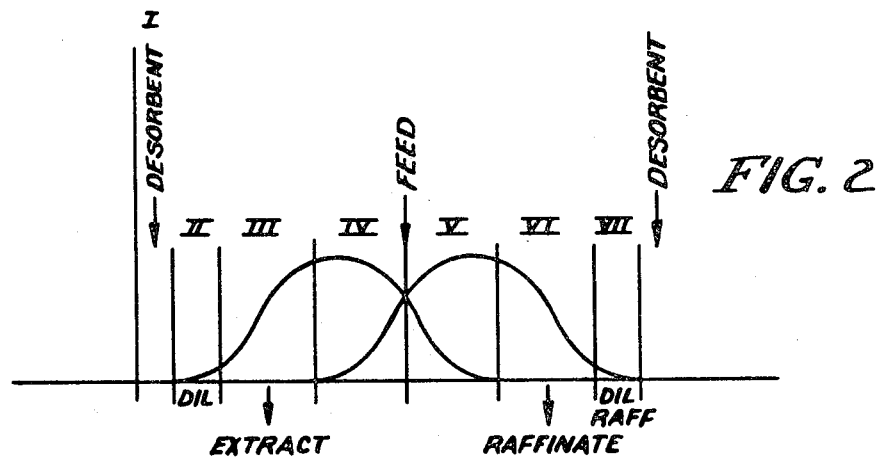
FIG. 2 is a plot of concentration gradients on which the high efficiency co-current simulated moving bed flow scheme is based.

The above plot, as shown in FIG. 2, for purposes of the present invention, is divided into seven specific zones, as indicated. The first zone (zone I) is that of pure (or the highest purity) displacement fluid (desorbent) which is the location in the system at which desorbent is introduced. The second zone (zone II) is that of extract component (component 1) diluted with desorbent. The third zone (zone III) is that of concentrated extract component. The fourth zone (zone IV) is that of impure extract or extract and raffinate component (component 2) mixture with the extract component being the major component. The fifth zone (zone V) is that of impure raffinate or extract and raffinate component mixture with the raffinate component being the major component. The sixth zone (zone VI) is that of concentrated raffinate component. The seventh zone (zone VII) is that of raffinate component diluted with desorbent.

The zones of FIG. 2 are established as a dynamic system in a series of separating units. The inlet stream to each zone and the feed stream inlet are analogous to the inlet streams of a series of separating units with the inlet streams of the units arranged in the same order as the inlets to the zones of FIG. 2. Thus, beginning arbitrarily with the feedstream as the inlet stream to a first separating unit (the separating units being numbered sequentially from left to right) and looking from right to left on the plot of FIG. 2, the inlet stream to the next or second separating unit would be that of zone IV, the inlet stream to a third separating unit would be that of zone II (zone III is for concentrated extract, a product stream, and as such has no inlet stream associated with it), the inlet stream to a fourth separating unit would be that of zone I, the inlet stream to a fifth separating unit would be that of zone VII (continuing at the opposite end of the plot, and again from right to left), and the inlet stream to a sixth separating unit would be that of zone V (zone VI is for concentrated raffinate, a product stream, and as such has no inlet stream associated with it).

Similarly, the outlet streams of the units are arranged in the same order as the outlets to the zones of FIG. 2. Thus, beginning arbitrarily with the zone IV outlet stream as the outlet stream to the first separating unit and looking from right to left on the plot of FIG. 2, the outlet stream to the second separating unit would be that of zone III (extract product), the outlet stream to the third separating unit would be that of zone II, the outlet stream to the fourth separating unit would be that of zone VII (zone I is the desorbent inlet, strictly an inlet stream, and as such has no outlet stream associated with it), the outlet stream to the fifth separating unit would be that of zone VI, and the outlet stream to the sixth separating unit would be that of zone V.

Figure 3:
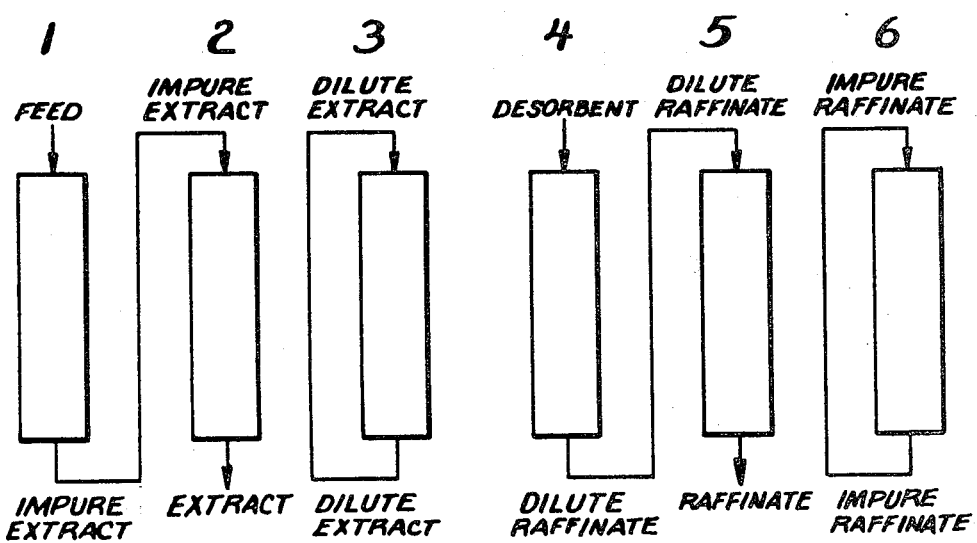
FIG. 3 is a flow diagram of the separating units of the co-current simulated moving bed embodiment of the present invention showing the various inlet and outlet streams and the location relationships of those streams for a particularly preferred configuration of that embodiment.

We look now to FIG. 3 for a schematic representation of the above six separating units (the units being numbered sequentially from left to right in accordance with the above discussion) and the associated inlet and outlet streams as established above. The sequence of the inlet streams and sequence of the outlet streams as shown are each fixed in accordance with the plot of FIG. 2 and will not vary. What may vary is the correspondence between the inlets and outlets of the separating units, since as stated above, the starting point in going through the sequence of inlet and outlet streams is arbitrary, e.g., if in the above discussion the outlet of zone III (concentrated extract) was specified as the outlet of the first separating unit, then each outlet as shown in FIG. 3 would be shifted one to the left with the zone IV outlet becoming the outlet of the sixth separating unit. There are, therefore, six possible combinations of the six separating unit embodiment, one of which is as shown in FIG. 3.

Another essential feature of the high efficiency simulated moving bed embodiment of the present invention is that inlets and outlets lying in the same zone are connected, as is also shown in FIG. 3, e.g., the outlet of the first separating unit is connected to the inlet of the second because that particular inlet and outlet both lie in zone IV. It should be noted with regard to the embodiment of the present invention shown in FIG. 3 that zones II and V lie in their entirety in the third and sixth separating units, respectively. The inlets and outlets of each of these two units are therefore connected to each other and the flow that occurs in both instances from these outlets to inlets is referred to as "pumparound". Those two embodiments of the invention having two separating units where pumparound occurs are the preferred embodiments.

Flow of fluids through the separating units, as indicated in FIG. 3, is continuous and unidirectional. In the course of such flow, the concentration gradient of FIG. 2 which occurs in the actual system is by no means static, but tends to progress as a wave (moving to the right) through the system and, therefore, the zones progress in a like manner. The various inlet and outlet streams would, thus, soon not be associated with the appropriate zones if some compensating means were not employed. The means employed are similar to those disclosed for the simulated moving bed in the above discussed U.S. Pat. No. 2,985,589 to Broughton et al., i.e., the inlets and outlets are periodically simultaneously shifted to keep pace with the progression of the curves. However unlike the simulated moving bed countercurrent flow systems of Broughton et al, the effect of the shifting in the present invention is a co-current movement of the beds with the fluid flow. The shifting effected is: the feed mixture inlet to what prior to the shift was the inlet of zone V, the inlet of zone V to what had been the inlet of zone VII, the inlet of zone VII to what had been the inlet of zone I, the inlet of zone I to what had been the inlet of zone II, the inlet of zone II to what had been the inlet of zone IV, the inlet of zone IV to what had been the feed mixture inlet, the outlet of zone II to what had been the outlet of zone III, the outlet of zone III to what had been the outlet of zone IV, the outlet of zone IV to what had been the outlet of zone V, the outlet of zone V to what had been the outlet of zone VI, the outlet of zone VI to what had been the outlet of zone VII, and the outlet of zone VII to what had been the outlet of zone II. The foregoing shifting should each time be carried out prior to the progression through the units of the component concentration distribution to the extent that the composition of the inlet or outlet streams to or from any zone becomes inconsistent with the desired composition of that zone.

Although both liquid and vapor phase operations can be used in many adsorptive separation processes, liquid-phase operation is required for this process because of the lower temperature requirements and because of the higher yields of extract product that can be obtained with liquid-phase operation over those obtained with vapor-phase operation. Adsorption conditions will include a temperature range of from about 20° C. to about 200° C. with about 20° C. to about 100° C. being preferred and a pressure range of from about atmospheric to about 500 psig with from about atmospheric to whatever pressure is required to ensure liquid phase being preferred. Desorption conditions will include the same range of temperatures and pressures as used for adsorption conditions.

The size of the units which can utilize the process of this invention can vary anywhere from those of pilot plant scale (see for example our assignee's U.S. Pat. No. 3,706,812) to those of commercial scale and can range in flow rates from as little as a few cc an hour up to many thousands of gallons per hour.

The following example is presented to illustrate the process of the present invention and is not intended to unduly restrict the scope and spirit of the claims attached hereto.

EXAMPLE

This example illustrates the ability of our process when operated in one preferred embodiment which utilizes a continuous simulated moving bed countercurrent type of operation, and comprises a pilot plant scale testing apparatus known as a carousel unit. The adsorption column was packed with potassium exchanged X-type zeolite and divided into eight beds. The feed composition was an aqueous solution containing 50 wt. % dry solids of which 75.5 wt. % was glucose with the remainder of dry solids being higher polysaccharides. The desorbent comprised deionized water. Other operating parameters, including product purity and recovery, were as follows:

| | |
|---|---|
| $A_1/F$ | 1.2 |
| $\theta$, hrs | 1.0 |
| $L_2/A$ | 1.30 |
| $L_3/A$ | 2.55 |
| $L_4/A$ | −0.05 |
| Wt. % Purity | 99.5 |
| Wt. % Recovery | 90.0 |

Where A is the selective pore volume circulations per hour, F is the feed rate; $\theta$ is the valve cycle time of the moving bed system; and $L_2$, $L_3$ and $L_4$ are the liquid flow rates into zones II, III and IV, respectively, less the void volume of each respective zone.

It should be mentioned at this point that the data presented in this example is scaled up from actual data obtained in the pilot plant to illustrate orders of magnitude that would be expected in a commercial operation for which the total bed volume if 6,000 feet$^3$. Furthermore, although optional buffer zone IV was not used in the pilot plant, data for a zone IV comprising one extra bed has been synthesized and integrated into the actual data.

The relevant data is as follows:

| MATERIAL BALANCE:* | | LBS/HR | | |
|---|---|---|---|---|
| | Feed | Ext | Raff | Desorb |
| Glucose | 15729 | 14156 | 1573 | |
| Polys | 5105 | 71 | 5034 | |
| Σ Solids | 20834 | 14227 | 6607 | |
| Water | 20833 | 42660 | 84433 | 106,260 |
| Total | 41667 | 56887 | 91040 | 106,260 |

| STREAM DATA - Operating Temperature 150° F. | | | | |
|---|---|---|---|---|
| | GPM @ 150° F. | WT % Solids | Sp. gr. | LB/Gal @ 150° F. |
| Feed | 69.31 | 50.0 | 1.224 | 10.02 |
| Extract | 103.96 | 25.0 | 1.113 | 9.12 |
| Raff | 181.59 | 7.26 | 1.021 | 8.36 |
| Desorb | 216.24 | -0- | | 8.19 |

| ZONE RATES AND BED CONFIGURATION | | |
|---|---|---|
| ZONE | Rate at 150° F. GPM | # of Beds in Zone |
| I | 717.4 | 2 |
| II | 648.1 | 4 |
| III | 752.1 | 2 |
| IV | 538.8 | 1 |
| | | 9 Total Beds/Chambers |

*For purposes of physical property estimation, the feed was assumed to be equivalent to 82 dextrose equivalent (DE) corn syrup and raffinate as 50 DE corn syrup. Data tables are available for these common corn syrups. Extract properties are those of dextrose solutions, which are also readily available.

The effectiveness of the present invention for extracting glucose from a glucose-polysaccharide mixture is clearly shown by the above data.

ILLUSTRATIVE EMBODIMENT

This illustration of the present invention is based on a computer simulation for the use of the above discussed high efficiency co-current simulated moving bed for the separation of glucose from an aqueous solution of glucose and polysaccharides. The separating units comprise columns packed with K-X type zeolite adsorbent having selectivity for glucose. The applicable flow scheme is that shown in FIG. 3.

Although the data associated with this Illustrative Embodiment is computer generated and based on a mathematical model, certain parameters comprising part of the computer input such as flow rates, feed composition, and degree of axial mixing, are as observed on an actual pilot plant not yet completely operable.

The following parameters apply for this illustration:
Feed Composition: 27.6 wt. % dry solids
   76.5 wt. % (based on dry solids) monosaccharides (96% glucose)
   8.3 wt. % di- and trisaccharides
   15.2 wt. % higher order saccharides
Desorbent: 100% water
Flow Rates:
   Feed/Extract: 4.95 cc/min
   Desorbent/Raffinate: 7.43 cc/min
   Recycle I: 3.58 cc/min
   Recycle II: 3.58 cc/min
Adsorbent Volume: 385.00 cc (each column)
Cycle Time: 60 minutes The cycle time is the time for a given column or separating unit to complete one full cycle through all the zones. A cycle is broken up into six steps of equal duration, in this case, therefore, ten minutes per step, the shifting of the various inlet and outlet streams occurring once at the end of each step.

Recycle I and Recycle II are the pump around flow rates of separating units 3 and 6, respectively, as shown in FIG. 3.

The selectivities of glucose with respect to di- and trisaccharides and with respect to water are 30.0 and 2.14 respectively. The selectivity of glucose with respect to the higher polysaccharides is essentially infinite.

Plug flow of liquids through the columns is not assumed, i.e., there is presumed to be a degree of axial mixing.

The computed plots of the composition of the effluent of one of the six columns throughout one full cycle is shown on FIG. 4. This particular column is in the column one position at the start of the cycle at which time its effluent comprises the extract output stream. Through the remainder of the cycle the column progresses sequentially to the second, third, fourth, fifth and sixth positions.

The purity of the extract stream as shown in FIG. 4 is 98.3% on a dry solids basis. The glucose recovery is 74.3%.

The above figures for purity and recovery are remarkable, even though not as good as the corresponding figures in the Example for a countercurrent system (99.5% and 90.0%, respectively), in view of the low dry solids content of the feed, i.e., 27.6 wt. %, as compared to 50.0 wt. % for the countercurrent system. The co-current system illustrated is required to obtain a high recovery from a relatively dilute feed solution, a far more difficult task. In fact, in spite of the dilution of the feed stream the co-current system uses only about 6.2 grams of desorbent per gram of glucose in the feed as compared to 6.76 grams per gram in the countercurrent system.

We claim as our invention:

1. A process for the recovery of glucose from a mixture thereof with polysaccharides which comprises contacting in liquid phase an aqueous mixture containing glucose and polysaccharides, at a temperature in the range of from 20° to 200° C. and at a pressure sufficient to maintain a liquid phase throughout separation, with an X zeolite containing potassium cations at exchangeable cationic sites and selectively adsorbing glucose in said zeolite, removing said polysaccharides from said zeolite, and thereafter recovering the adsorbed glucose from the zeolite by means of a desorbent liquid at a temperature in the range of from 20° to 200° C. and at a pressure sufficient to maintain a liquid phase throughout separation.

2. The process of claim 1 wherein said glucose is recovered from said zeolite by desorption with a desorbent material comprising water.

3. The process of claim 1 wherein said process is effected with a simulated moving-bed flow system.

4. The process of claim 3 wherein said simulated moving-bed flow system is of the countercurrent type.

5. The process of claim 3 wherein said simulated moving-bed flow system is of the co-current high efficiency type.

6. The process of claim 1 wherein said zeolite is bound in a water-permeable organic polymer matrix.

7. The process of claim 1 wherein said zeolite is bound in an inorganic oxide matrix.

* * * * *